(12) United States Patent
Brady et al.

(10) Patent No.: US 7,025,783 B2
(45) Date of Patent: Apr. 11, 2006

(54) ACCOMMODATING INTRAOCULAR LENS WITH INTEGRAL CAPSULAR BAG RING

(75) Inventors: Daniel G. Brady, San Juan Capistrano, CA (US); Stephen W. Laguette, Laguna Niguel, CA (US); Marlene L. Paul, Laguna Niguel, CA (US); Elbert Y. Tzeng, Irvine, CA (US); Robert E. Glick, Lake Forest, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 85 days.

(21) Appl. No.: 10/341,701

(22) Filed: Jan. 14, 2003

(65) Prior Publication Data

US 2003/0135272 A1  Jul. 17, 2003

Related U.S. Application Data

(60) Provisional application No. 60/348,705, filed on Jan. 14, 2002, provisional application No. 60/372,309, filed on Apr. 12, 2002.

(51) Int. Cl.
*A61F 2/16* (2006.01)

(52) U.S. Cl. .................. 623/6.22; 623/6.24; 623/6.47; 623/6.49

(58) Field of Classification Search ............. 623/6.11, 623/6.13, 6.14, 6.15, 6.17, 6.18, 6.19, 6.2, 623/6.21, 6.22, 6.24, 6.38, 6.4, 6.43, 6.46, 623/6.47, 6.49, 6.51, 6.52, 6.53, 6.54
See application file for complete search history.

(56) References Cited

U.S. PATENT DOCUMENTS

| 1,483,509 | A | 2/1924 | Bugbee |
|---|---|---|---|
| 2,129,305 | A | 9/1938 | Feinbloom |
| 2,274,142 | A | 2/1942 | Houchin |
| 2,405,989 | A | 6/1946 | Beach |
| 2,511,517 | A | 6/1950 | Spiegel |
| 3,004,470 | A | 10/1961 | Ruhle |
| 3,031,927 | A | 5/1962 | Wesley |

(Continued)

FOREIGN PATENT DOCUMENTS

| AU | 3225789 | 10/1989 |
|---|---|---|

(Continued)

OTHER PUBLICATIONS

Menzo et al. J Cataract Refract. Surg 24, Aug. 1998.

(Continued)

*Primary Examiner*—Corrine McDermott
*Assistant Examiner*—Thomas J Sweet
(74) *Attorney, Agent, or Firm*—Advanced Medical Optics, Inc.

(57) ABSTRACT

An intraocular lens (IOL) includes an optic for focusing light, an outer ring for supporting the optic in a capsular bag of an eye and a plurality of radially spaced apart, elongated intermediate members connecting the optic to the outer ring. The intermediate members are configured to convert radial forces exerted by the capsular bag on the support ring into axial movement of the optic, allowing a presbyopic patient to more effectively focus on near objects. The outer ring is preferably contoured to conform to the portion of the capsular bag between the anterior and posterior zonules, and has sufficient axial thickness to contact both sets of zonules. In addition, the edge of the ring includes at least one sharp edge corner to prevent epithelial cell growth toward the optic. In addition, the outer ring may include weakened areas configured to allow consistent and repeatable deformation in response to compressive forces.

3 Claims, 7 Drawing Sheets

U.S. PATENT DOCUMENTS

| | | |
|---|---|---|
| 3,034,403 A | 5/1962 | Neefe |
| RE25,286 E | 11/1962 | Decarle |
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,693,301 A | 9/1972 | Lemaltre |
| 3,794,414 A | 2/1974 | Wesley |
| 3,922,728 A | 12/1975 | Krasnov |
| 3,932,148 A | 1/1976 | Krewalk, Sr. |
| 4,055,378 A | 10/1977 | Feneberg et al. |
| 4,062,629 A | 12/1977 | Winthrop |
| 4,073,579 A | 2/1978 | Deeg et al. |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Gullino et al. |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert, Jr. |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A * | 1/1984 | Schlegel ................ 623/6.4 |
| 4,442,553 A | 4/1984 | Hessburg |
| 4,463,458 A | 8/1984 | Seidner |
| 4,476,591 A | 10/1984 | Arnott |
| 4,504,981 A | 3/1985 | Walman |
| 4,504,982 A | 3/1985 | Burk |
| 4,512,040 A | 4/1985 | McClure |
| 4,551,864 A | 11/1985 | Akhavi |
| 4,560,383 A | 12/1985 | Leiske |
| 4,573,775 A | 3/1986 | Bayshore |
| 4,573,998 A * | 3/1986 | Mazzocco ................ 128/898 |
| 4,575,878 A | 3/1986 | Dubroff |
| 4,580,882 A | 4/1986 | Nuchman et al. |
| 4,581,033 A | 4/1986 | Callahan |
| 4,596,578 A | 6/1986 | Kelman |
| 4,617,023 A | 10/1986 | Peyman |
| 4,618,228 A | 10/1986 | Baron et al. |
| 4,618,229 A | 10/1986 | Jacobstein et al. |
| 4,629,460 A | 12/1986 | Dyer |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,676,792 A | 6/1987 | Praeger |
| 4,687,484 A | 8/1987 | Kaplan |
| 4,693,572 A | 9/1987 | Tsuetaki et al. |
| RE32,525 E | 10/1987 | Pannu |
| 4,702,244 A | 10/1987 | Mazzocco |
| 4,704,016 A | 11/1987 | DeCarle |
| 4,720,286 A | 1/1988 | Bailey et al. |
| 4,725,278 A | 2/1988 | Shearing |
| 4,752,123 A | 6/1988 | Blaker |
| 4,759,762 A | 7/1988 | Grendahl |
| 4,769,033 A | 9/1988 | Nordan |
| 4,787,903 A | 11/1988 | Grendahl |
| 4,790,847 A | 12/1988 | Woods |
| 4,813,955 A | 3/1989 | Achatz et al. |
| 4,816,032 A | 3/1989 | Hetland |
| 4,830,481 A | 5/1989 | Futhey et al. |
| 4,840,627 A | 6/1989 | Blumenthal |
| 4,842,601 A | 6/1989 | Smith |
| 4,878,911 A * | 11/1989 | Anis ................ 623/6.42 |
| 4,881,804 A | 11/1989 | Cohen |
| 4,888,012 A | 12/1989 | Horn et al. |
| 4,888,015 A | 12/1989 | Domino |
| 4,888,016 A | 12/1989 | Langerman |
| 4,890,912 A | 1/1990 | Visser |
| 4,890,913 A | 1/1990 | DeCarle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell et al. |
| 4,938,583 A | 7/1990 | Miller |
| 4,955,902 A | 9/1990 | Kelman |
| 4,976,534 A | 12/1990 | Miege et al. |
| 4,976,732 A | 12/1990 | Vorosmarthy |
| 4,990,159 A | 2/1991 | Kraff |
| 4,994,082 A | 2/1991 | Richards et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,129,718 A | 7/1992 | Futhey et al. |
| 5,147,397 A | 9/1992 | Christ et al. |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |
| RE34,998 E | 7/1995 | Langerman |
| 5,443,506 A | 8/1995 | Garabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,521,656 A | 5/1996 | Portney |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,628,795 A | 5/1997 | Langerman |
| 5,628,796 A | 5/1997 | Suzuki |
| 5,628,797 A | 5/1997 | Richer |

| | | |
|---|---|---|
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,766,244 A | 6/1998 | Binder |
| 5,769,890 A | 6/1998 | McDonald |
| 5,776,191 A | 7/1998 | Mazzocco |
| 5,776,192 A | 7/1998 | McDonald |
| 5,814,103 A | 9/1998 | Lipshitz et al. |
| 5,824,074 A | 10/1998 | Koch |
| 5,843,188 A | 12/1998 | McDonald |
| 5,847,802 A | 12/1998 | Meneles et al. |
| 5,876,442 A | 3/1999 | Lipshitz et al. |
| 5,898,473 A | 4/1999 | Seidner et al. |
| 6,013,101 A | 1/2000 | Israel |
| 6,051,024 A | 4/2000 | Cumming |
| 6,096,078 A | 8/2000 | McDonald |
| 6,110,202 A | 8/2000 | Barraquer et al. |
| 6,117,171 A | 9/2000 | Skottun |
| 6,136,026 A * | 10/2000 | Israel ................... 623/6.11 |
| 6,176,878 B1 | 1/2001 | Gwon et al. |
| 6,197,058 B1 | 3/2001 | Portney |
| 6,217,612 B1 | 4/2001 | Woods |
| 6,231,603 B1 | 5/2001 | Lang et al. |
| 6,299,641 B1 | 10/2001 | Woods |
| 6,322,589 B1 | 11/2001 | Cumming |
| 6,406,494 B1 | 6/2002 | Laguette et al. |
| 6,443,985 B1 | 9/2002 | Woods |
| 6,485,516 B1 * | 11/2002 | Boehm ................... 623/6.49 |
| 6,524,340 B1 * | 2/2003 | Israel ................... 623/6.44 |
| 6,551,354 B1 * | 4/2003 | Ghazizadeh et al. ....... 623/6.43 |
| 6,554,859 B1 * | 4/2003 | Lang et al. ............ 623/6.28 |
| 6,592,621 B1 | 7/2003 | Domino |
| 6,599,317 B1 | 7/2003 | Weinschenk, III et al. |
| 6,638,305 B1 | 10/2003 | Laguette |
| 6,749,633 B1 * | 6/2004 | Lorenzo et al. ............ 623/6.36 |
| 6,749,634 B1 * | 6/2004 | Hanna ................... 623/6.37 |
| 2002/0116058 A1 | 8/2002 | Zadno-Azizi et al. |
| 2002/0188351 A1 | 12/2002 | Laguette |
| 2003/0135272 A1 | 7/2003 | Brady et al. |
| 2004/0082993 A1 | 4/2004 | Woods |
| 2004/0082994 A1 | 4/2004 | Woods et al. |

FOREIGN PATENT DOCUMENTS

| | | |
|---|---|---|
| DE | 2702117 | 7/1978 |
| EP | 0064812 | 11/1982 |
| EP | 0246216 | 11/1987 |
| EP | 0329981 | 8/1989 |
| EP | 0337390 | 10/1989 |
| EP | 0342895 | 11/1989 |
| EP | 0351471 | 1/1990 |
| EP | 0488835 | 6/1992 |
| EP | 0507292 | 10/1992 |
| EP | 0566170 | 10/1993 |
| EP | 0601845 | 6/1994 |
| EP | 0691109 | 1/1996 |
| EP | 0897702 | 2/1999 |
| GB | 2058391 | 4/1981 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |
| WO | 8603961 | 7/1986 |
| WO | 8700299 | 1/1987 |
| WO | 8707496 | 12/1987 |
| WO | 8902251 | 3/1989 |
| WO | 8911672 | 11/1989 |
| WO | 9000889 | 2/1990 |
| WO | 9416648 | 8/1994 |
| WO | 9503783 | 2/1995 |
| WO | 9610968 | 4/1996 |
| WO | 9615734 | 5/1996 |
| WO | 9625126 | 8/1996 |
| WO | 9712272 | 4/1997 |
| WO | 9727825 | 8/1997 |
| WO | 9743984 | 11/1997 |
| WO | 9856315 | 12/1998 |
| WO | 0066039 | 11/2000 |
| WO | WO 01/19288 A1 | 3/2001 |
| WO | 0134067 | 5/2001 |
| WO | WO 01/34066 * | 5/2001 |
| WO | WO 02/19949 A2 | 3/2002 |
| ZA | 888414 | 11/1988 |

OTHER PUBLICATIONS

Fechner et al. J Cataract Refract. Surg 24, Jan. 1998.
Amo Specs. Model AC-218, 1992.
Chiron Vision, Nuvita MA20, 1997.
Mandell, Contact Lens Practice, 4$^{TH}$ Ed.
Partial Program Re: ASCRS Symposium, Showing Video Tape Shown Between Apr. 10-14, 1999.
Video Tape "New Elliptical Accom. Iol for Cataract Surgery" Shown at ASCRS Symposium on Apr. 10, 1999.
Thornton, Accommodation in Pseudophakia 25, P159.
U.S. Appl. No. 09/390,380, filed Sep. 3, 1999.
U.S. Appl. No. 09/522,326, filed Mar. 9, 2000.
U.S. Appl. No. 09/532,910, filed Mar. 22, 2000.
U.S. Appl. No. 09/565,036, filed May 3, 2000.
U.S. Appl. No. 09/631,223, filed Aug. 2, 2000.
U.S. Appl. No. 09/657,325, filed Sep. 7, 2000.
U.S. Appl. No. 09/656,661, filed Sep. 7, 2000.
U.S. Appl. No. 09/657,251, filed Sep. 7, 2000.
U.S. Appl. No. 09/721,072, filed Nov. 22, 2000.
U.S. Appl. No. 09/795,929, filed Feb. 28, 2001.
U.S. Appl. No. 09/822,040, filed Mar. 30, 2001.

* cited by examiner

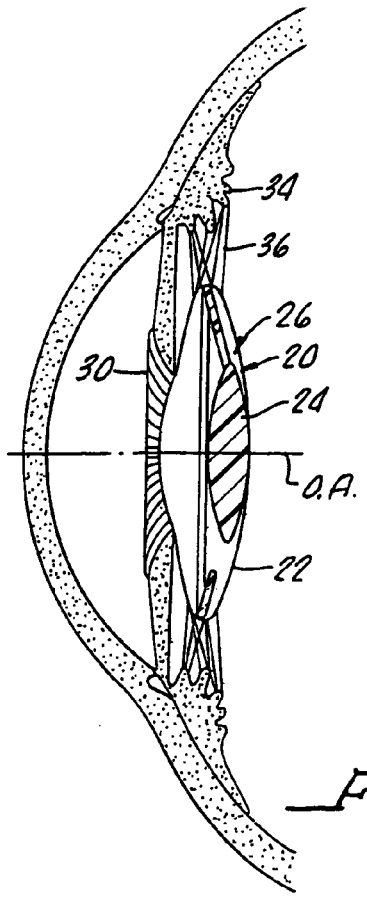
FIG. 1.
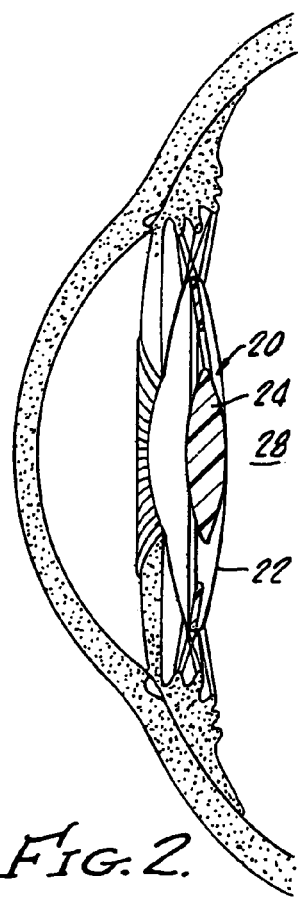
FIG. 2.
FIG. 3.
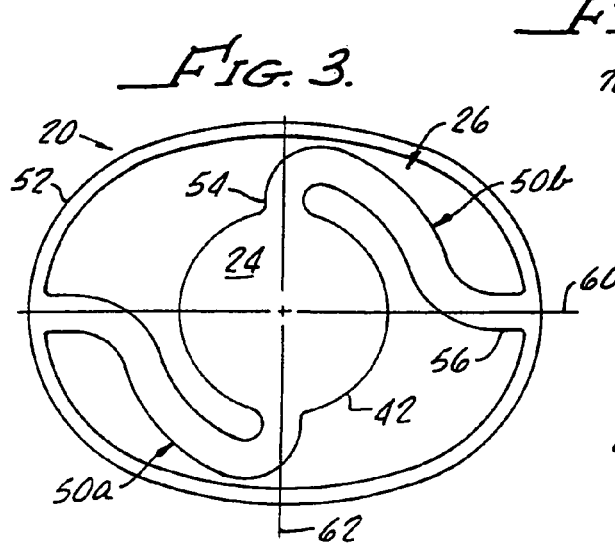
FIG. 4.
FIG. 5.
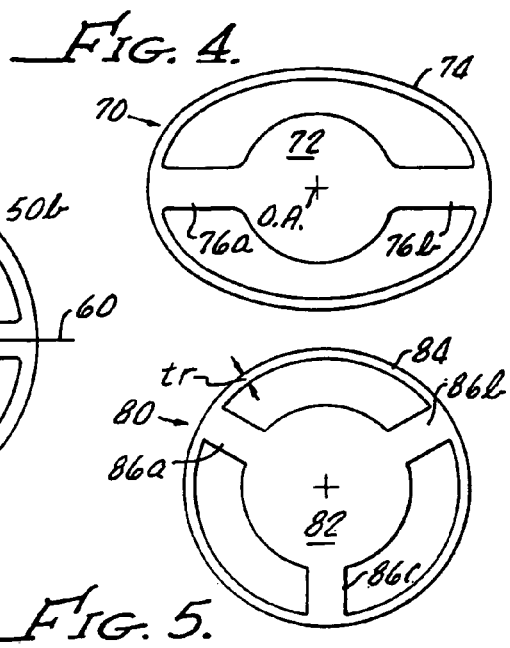

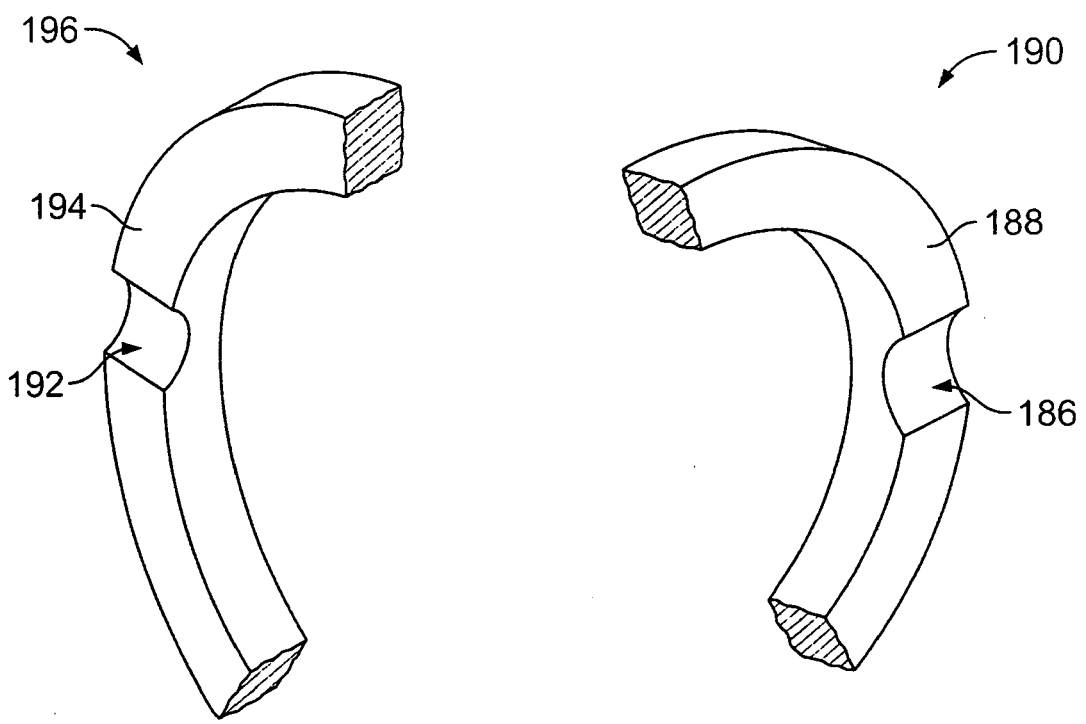
FIG. 15  FIG. 16
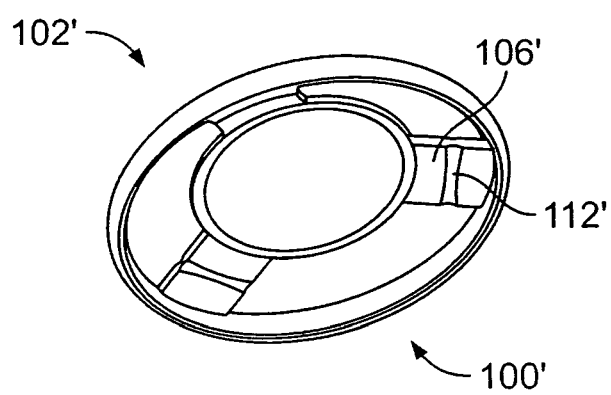
FIG. 17

ACCOMMODATING INTRAOCULAR LENS WITH INTEGRAL CAPSULAR BAG RING

This application claims the benefit of provisional application Ser. No. 60/348,705, filed Jan. 14, 2002, and provisional application Ser. No. 60/372,309, filed Apr. 12, 2002. The disclosure of each of these provisional applications is incorporated in its entirety herein by reference.

BACKGROUND OF THE INVENTION

The present invention relates to intraocular lenses (IOLs). More particularly, the present invention relates to IOLs that provide accommodating movement in the eye.

The human visual system includes the eyes, the extraocular muscles which control eye position within the eye socket, the optic and other nerves that connect the eyes to the brain, and particular areas of the brain that are in neural communication with the eyes. Each eye forms an image upon a vast array of light sensitive photoreceptors of the retina. The cornea is the primary refracting surface which admits light through the anterior part of the outer surface of the eye. The iris contains muscles which alter the size of the entrance port of the eye, or pupil. The crystalline lens has a variable shape within the capsular bag, under the indirect control of the ciliary muscle. Having a refractive index higher than the surrounding media, the crystalline lens gives the eye a variable focal length, allowing accommodation to objects at varying distances from the eye.

Much of the remainder of the eye is filled with fluids and materials under pressure which help the eye maintain its shape. For example, the aqueous humor fills the anterior chamber between the cornea and the iris, and the vitreous humor fills the majority of the volume of the eye in the vitreous chamber behind the lens. The crystalline lens is contained within a third chamber of the eye, the posterior chamber, which is positioned between the anterior and vitreous chambers.

The human eye is susceptible to numerous disorders and diseases, a number of which attack the crystalline lens. For example, cataracts mar vision through cloudy or opaque discoloration of the lens of the eye. Cataracts often result in partial or complete blindness. If this is the case, the crystalline lens can be removed and replaced with an intraocular lens, or IOL.

While restoring vision, conventional IOLs have limited ability for accommodation (i.e., the focusing on near objects). This condition is known as presbyopia. To overcome presbyopia of an IOL, a patient may be prescribed eyeglasses. Alternative attempts in the art to overcome presbyopia focus on providing IOLs with accommodation ability. Accommodation may be accomplished by either changing the shape of the IOL, e.g., to become more convex to focus on near objects, or by moving the IOL along its optical axis. Examples of this latter approach are disclosed in Gwon et al. U.S. Pat. No. 6,176,878 and Laguette et al. U.S. Pat. No. 6,406,494. The disclosures of both these patents are incorporated herein in their entirety by reference.

In a healthy eye, accommodation is achieved through the actions of the ciliary muscles as well as through changes in the pressure exerted by vitreous fluids on the capsular bag. Prior art accommodating IOLs have typically attempted to take advantage of one of these two naturally occurring mechanisms. For instance, one class of accommodating IOL takes advantage of changes in the pressure of the vitreous fluids by placing the optic of the IOL in direct contact with the posterior wall of the capsular bag. Thus, axial forces on the capsular bag are transmitted directly to the optic. Another class of accommodating IOL takes advantage of the actions of the ciliary muscles by circumscribing the optic with a flexible, anteriorly vaulted movement assembly that converts radial forces on the capsular bag into axial movement of the optic.

IOLs which use primarily only one of these two naturally occurring mechanisms have a tendency to provide insufficient forward axial movement to achieve full range accommodation.

In addition, some of the prior art accommodating IOL designs include relatively stiff outer rings for supporting the IOL in the capsular bag of the eye. These outer rings add stability to the design. However, research has shown that in some designs, the ring may buckle or bend when the capsular bag is compressed. Unfortunately, the buckling or bending does not occur in a predictable or reliable fashion. In other words, a ring may buckle in one location at one time, and in another location another time. Because of this, the compression and movement characteristics of the IOL are inconsistent, and tilting and other undesirable outcomes may occur.

In view of the foregoing, it would be beneficial in the art, and there continues to be a need, to provide new IOLs adapted for sufficient accommodation to overcome or significantly reduce the effects of presbyopia.

SUMMARY OF THE INVENTION

In accordance with the present invention, an intraocular lens for insertion into a capsular bag of an eye comprises an optic, an outer ring surrounding the optic, and movement assembly including a plurality of intermediate members that extend between the optic and the outer ring and transmit forces therebetween. The optic preferably has a circular periphery centered on an optical axis and is adapted to focus light toward a retina of an eye and to provide a vision correction. The outer ring is spaced from the optic with voids therebetween.

The outer ring may be either circular or ovoid in configuration. In embodiments having a circular outer ring, the intermediate members are preferably distributed asymmetrically about any plane that includes the optical axis. For instance, in one preferred embodiment, three intermediate members are arranged at 120° intervals around the circumference of the ring. In embodiments having an oval outer ring, there are preferably only two diametrically opposed intermediate members.

In the case of an oval outer ring, the ring has a major axis and a minor axis. In one embodiment of the invention, the outer end of each intermediate member is secured to the outer ring at a point on the major axis, and the inner end is secured to the periphery of the optic at a point on the minor axis. In other words, the intermediate members are non-linear, and the inner and outer ends are displaced by 90° with respect to one another. In another embodiment, the inner and outer ends are both aligned with the major axis.

Each intermediate member may have a hinge therein that permits radial forces imparted by the surrounding eye structure, e.g. muscles, to more effectively translate the optic along the optical axis. The hinges may have any suitable structure effective to provide such enhanced translation relative to a substantially identical IOL including intermediate members without hinges, such as an IOL with uniformly structured intermediate members. A typical hinge structure may include a reduced axial or circumferential thickness region along a plate-like intermediate member.

Preferably, the outer ring has an outer surface that is convexly outwardly curved to match the contour of the interface between the capsular bag and the zonules of the eye. In addition, the outer ring may have at least one relatively sharp edge to reduce epithelial cell growth thereon. In addition, the outer ring may be continuous and have an axial thickness of at least 0.4 mm. Desirably, the optic, outer ring and intermediate members are integrally formed, for example molded, of a single piece of material.

In one embodiment, the outer ring has an axial dimension and the intermediate members attach to a posterior edge of the outer ring. Furthermore, the intermediate members may be bowed in the posterior direction, causing the optic to be posteriorly vaulted.

In accordance with still another embodiment, the support ring of the IOL is structured to result in consistent bending and movement of the ring in response to compressive forces. The improved ring structure includes weakening means, such as thinned areas, grooves, notches or hinges to allow consistent and repeatable deformation during compression. The weakening means may positioned to cause bending in an inward, outward, posterior, or anterior direction, or any combination of these. Ideally, the weakening means are located symmetrically within the ring, and are located opposite the intermediate members.

Each and every feature described herein, and each and every combination of two or more of such features, is included within the scope of the present invention provided that the features included in such a combination are not mutually inconsistent.

Additional aspects, features, and advantages of the present invention are set forth in the following description and claims, particularly when considered in conjunction with the accompanying drawings in which like parts bear like reference numbers.

BRIEF DESCRIPTION OF THE DRAWINGS

FIG. 1 is a vertical cross-section of an eye illustrating an exemplary intraocular lens of the present invention positioned within the capsular bag;

FIG. 2 is a cross-section similar to FIG. 1 showing forward or anterior movement of an optic of the intraocular lens;

FIG. 3 is a plan view of the exemplary intraocular lens of the present invention having an oval outer ring and a pair of nonlinear intermediate members;

FIG. 4 is a plan view of an alternative intraocular lens of the present invention having two radially oriented intermediate members;

FIG. 5 is a plan view of an alternative intraocular lens of the present invention having three radially oriented intermediate members;

FIG. 15 is a fragmentary perspective posterior view showing a portion of a support ring structured to bend in an anterior direction;

FIG. 16 is a fragmentary perspective anterior view showing a support ring structured to bend in a posterior direction;

FIG. 17 is a view similar to FIG. 7B, showing an embodiment of the invention having an alternate hinge configuration;

DESCRIPTION OF THE PREFERRED EMBODIMENTS

Figure 6:
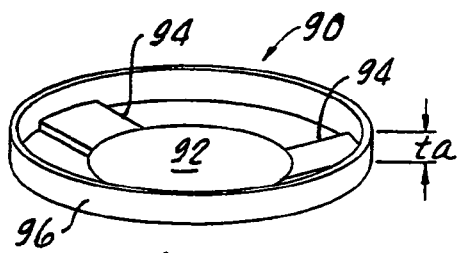
FIG. 6 is a perspective view of an alternative intraocular lens of the present invention having three radially oriented intermediate members.

Referring to the drawings in more detail, an intraocular lens (IOL) 20 according to an exemplary embodiment of the present invention is illustrated in FIGS. 1 and 2 after implantation in the capsular bag 22 of an eye. Exemplary IOL 20 includes an optic 24 and a movement assembly 26 coupled thereto. The optic 24, which has an optical axis OA, is adapted to focus light onto a retina of an eye. The movement assembly 26 of exemplary IOL 20 cooperates with the eye to effect accommodating movement of the optic 24 and, in particular, converts radial movement (i.e., movement perpendicular to the optical axis OA) of the capsular bag of an eye to axial movement (i.e., movement parallel to the optical axis OA) of the optic 24. In the exemplary embodiment, the movement assembly 26 biases the optic 24 in a posterior direction (to the right) against the posterior wall of the capsular bag 22.

A brief description of the anatomy of the eye is appropriate in order to understand the invention. The capsular bag 22 resides in the posterior chamber of the eye and is in direct contact with the jelly-like vitreous humor 28 which fills the nearly spherical space between the capsular bag and the retina (not shown). In a healthy person, the capsular bag 22 contains the natural crystalline lens which transmits light passing through the orifice of the iris 30 to the retina. The capsular bag 22 is connected to an annular ciliary muscle 34 by suspensory ligaments or zonules 36. The ciliary muscle 34 is the chief agent in accommodation, i.e., in adjusting the eye to focus on near objects. The zonules 36 retain the lens in position and are relaxed by the contraction of the ciliary muscle 34, thereby allowing a natural crystalline lens to become more convex.

Applying this anatomy to the present invention, exemplary IOL 20 is configured to facilitate movement of the optic 24 in response to the action of the ciliary muscle 34 and the zonules 36. When the ciliary muscle 34 constricts inward, the zonules 36 relax and reduce the equatorial diameter of the capsular bag 22, wherein the optic 24 translates in the posterior direction against the rear wall of the capsular bag 22. Conversely, when the ciliary muscle 34 relaxes, the zonules 36 tense and increase the equatorial diameter of the capsular bag 22, thereby moving the optic 24 in the anterior direction, or at least reducing the posterior bias.

It should be understood that, in the illustrated embodiment, the optic 24 is biased against the rear wall of the capsular bag 22 at all times, and axial movement of the optic from the action of the ciliary muscle 34 is primarily governed by the position of the rear wall. That is, changes in pressure of the vitreous humor 28 act on the rear wall of the capsular bag 22 and cause it to translate in the axial direction. This movement is facilitated by relaxation of the ciliary muscle 34, which at least reduces the rearward bias of the optic 24. For example, FIG. 2 illustrates forward movement of the optic 24 due to increase in pressure of the vitreous humor 28. One advantage of the present invention is that the optic 24 remains biased against the rear wall of the capsular bag 22 yet can accommodate substantial forward or anterior movement because of long intermediate members.

FIG. 3 illustrates the exemplary IOL 20 in plan view, wherein a generally circular periphery or peripheral edge 42 defines the radially outer extent of the optic 24 and separates a posterior face from an anterior face. The optic 24 is typically circular, but may exhibit a different shape as long as the optical correction character is centered about the optical axis OA. The optic 24 may be bi-convex, or the anterior and posterior faces can take other shapes, such as planar or concave. In any event, the posterior face and anterior face are spaced apart on opposite sides of an optic plane (not shown) that extends perpendicular to the optical axis OA. In other words, the optic 24 is centered on and oriented in the optic plane.

In a preferred embodiment, the optic 24 is a multifocal optic having a plurality of zones of varying optical powers, wherein the maximum add power of the "near" zones is reduced by an amount equivalent to the diopter shift obtained through axial movement of the optic 24. Thus, the net power correction in the near zones is equal to the patient's full add prescription only when optic 24 has moved to the near distance (i.e. anteriormost) position. Examples of suitable multifocal optics are disclosed in Lang et al. U.S. Pat. No. 6,231,603 and Lang et al. PCT International Application No. WO/01/82839 A1. The disclosures of both the U.S. patent and the PCT international application are incorporated in the entirety herein by reference.

The movement assembly 26 comprises a pair of intermediate members 50a, 50b connected to and extending between the circular periphery 42 of the optic 24 and an outer ring 52. Each intermediate member 50a, 50b has an inner end 54 connected to the circular periphery 42, and an outer end 56 connected to the outer ring 52. "Connected" in this sense means firmly attached to with adhesive or ultrasonic bonding, or preferably formed integrally, or as a cohesive single piece. In the latter case, the lens is desirably molded. Each intermediate member 50a, 50b is desirably oriented in a plane that is in the optic plane. Indeed, the intermediate members 50a, 50b and outer ring 52 may have approximately the same thickness and be located in the same plane.

Although controlled fibrosis (i.e., cellular growth) on the outer ring 52 may be desirable, the IOLs 20 of the invention inhibit cell growth, particularly epithelial cell growth, onto the optic 24. This is accomplished by configuring the periphery 42 of the optic 24 with mechanical barriers such as relatively sharp posterior and/or anterior edge corners. The proliferation of unwanted epithelial cell growth may also be inhibited through the use of material properties.

The intermediate members 50a, 50b of the IOL 20 are substantially longer than previous intermediate members as they extend in a nonlinear fashion from the outer ring 52 to the circular optic periphery 42. More particularly, the inner end 54 and outer end 56 are angularly spaced about the optical axis OA by at least approximately 90°. The midportion of each intermediate member 50 extends in a serpentine fashion between its inner and outer ends.

In a preferred embodiment, as seen in FIG. 3, the outer ring 52 is oval in shape and has a major axis 60 perpendicular to the optical axis OA. A minor axis 62 extends perpendicularly to the major axis 60 and to the optical axis OA. Desirably, the outer ends 56 of the intermediate members 50 connect to the oval ring 52 along the major axis 60. In this way, the length of the intermediate members 50 is maximized. In the illustrated embodiment, the inner ends 54 of the intermediate members 50 connect to the circular optic periphery 42 along the minor axis 62. Therefore, the inner and outer ends 54, 56 are angularly spaced apart by about 90°.

FIG. 4 illustrates an alternative IOL 70 of the present invention having an optic 72, an oval outer ring 74, and a pair of intermediate members 76a, 76b extending radially therebetween. Again, the optic 72, outer ring 74 and intermediate members 76a, 76b are desirably formed as a single homogeneous (i.e., integral) piece. The oval outer ring 74 is believed to move the optic 72 axially with greater effectiveness than a circular ring because of the orientation of the intermediate members 76a,b along the major axis.

The fixation members 76a,b are shown as plate-like, and desirably are greater in width (the dimension parallel to the minor axis) than axial thickness (the dimension parallel to the optical axis). Preferably, the ratio of width to axial thickness is about four. In absolute terms, the width of the fixation members 76a, 76b may be between about 0.8 mm and about 3.0 mm.

FIG. 5 illustrates a still further IOL 80 having an optic 82, an outer ring 84, and three evenly arranged and radially oriented intermediate members 86a, 86b and 86c. Because the intermediate members 86 are not symmetric about any plane through the optical axis OA, forces exerted by the surrounding capsular bag do not act in opposition to one another and thus are translated more effectively into axial movement of the optic 82. The radial thickness $t_r$ of the outer ring 84 is indicated, and is desirably in the range of 0.2–0.6 mm. Moreover, the corners, or at least one corner, of the outer peripheral edge of the outer ring 84 are desirably relatively sharp to reduce the instance of epithelial cell growth thereon.

Figure 6A:
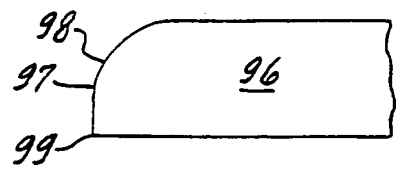
FIG. 6A is an elevational view of one edge of the intraocular lens of FIG. 6.

FIGS. 6 and 6A illustrate a still further IOL 90 having an optic 92, a plurality of intermediate members 94 extending radially outward therefrom, and an outer ring 96. The edge surface 97 of the outer ring 96 may be contoured to conform to the inner wall of the capsular bag. Therefore, as seen in FIG. 6A, at least a portion 98 of the edge surface 97 is convexly outwardly curved. At the same time, at least one corner, in this case the posterior corner 99, is left sharp (i.e. unpolished) to form a barrier against posterior capsular opacification (PCO).

Furthermore, FIG. 6 illustrates the greater axial thickness $t_a$ of the outer ring 96 with respect to the axial thickness of the intermediate members 94 and optic 92. Specifically, the axial thickness $t_a$ of the outer ring 96 is desirably between about 0.4 mm and about 1.0 mm. Without wishing to limit the invention to any particular theory of operation, it is believed that a ring having an axial thickness in this range will place both the posterior and the anterior zonules of the eye under tension. Thus, both sets of zonules work in unison to change the diameter of the capsular bag in response to action of the ciliary muscle, resulting in axial movement of the optic. A thinner ring would not interact as effectively with both sets of zonules, and thus, in all likelihood, would result in less axial movement.

In addition, an outer ring 96 having increased axial thickness will increase the pressure on the sharp corner 99 of the edge surface 97 to increase the barrier effect of the ring against PCO.

FIGS. 7A–7E show another IOL 100 of the present invention having a circular outer capsular bag support ring 102, an inner optic 104, and a movement system comprising a plurality of radially-oriented plate-like intermediate members 106 extending therebetween. Preferably, the optic 104, whether it be bi-convex or otherwise, is circumscribed by a circular rim 105 to which the fixation intermediate members 106 are directly attached. The rim 105 desirably has a constant axial dimension and helps to reduce glare while not increasing incision size.

Movement systems other than that shown may be suitable, such as a more solid interface rather than discrete intermediate members. However, separated intermediate members with voids therebetween and between the optic 104 and support ring 102 are preferred. The support ring 102, inner optic 104, and intermediate members 106 are firmly attached to each other with adhesive or ultrasonic bonding, or preferably formed integrally, i.e., molded or machined as one cohesive (homogeneous) piece of material. The IOL 100 is desirably liquid injection molded from silicone or machined from a hydrophilic material which fabrication process reduces cost and increases quality and/or consistency of the product.

Figure 7A:
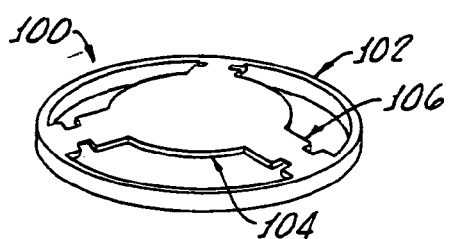
FIG. 7A is a perspective posterior view of a still further alternative intraocular lens of the present invention having three radially oriented plate-like intermediate members and an optic that is bowed slightly out of the plane of a surrounding capsular bag support ring.
Figure 7B:
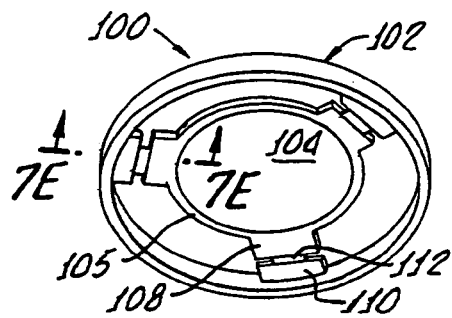
FIG. 7B is a perspective anterior view of the intraocular lens of FIG. 7A.

FIG. 7A illustrates the IOL 100 from the posterior side, while FIG. 7B is an anterior view. These two views show the axial position at which the intermediate members 106 attach to the support ring 102. That is, the support ring 102 has an axial dimension and the intermediate members 106 attach to a posterior edge thereof. When implanted, the intermediate members 106 and connected optic 104 are therefore held in a posterior-most position with respect to the support ring 102.

As in the embodiment of FIG. 6, the edge surface of the outer ring 102 is contoured to facilitate implantation within the capsular bag of the patient. More particularly, the support ring 102 has an outer surface that is convexly curved to better mate with the concave inner wall portion of the capsular bag between the anterior and posterior zonules.

Figure 7C:
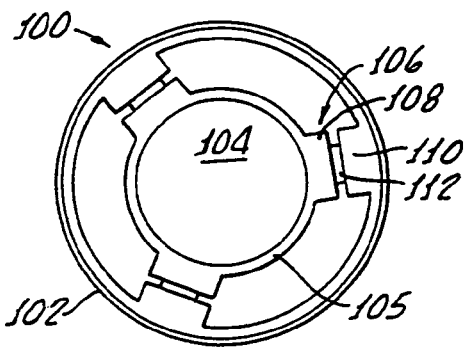
FIGS. 7C and 7D are plan and side elevational views, respectively, of the intraocular lens of FIG. 7A.
Figure 7D:
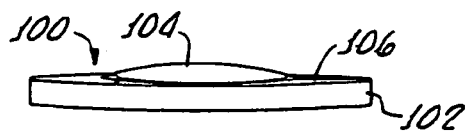
Figure 7E:
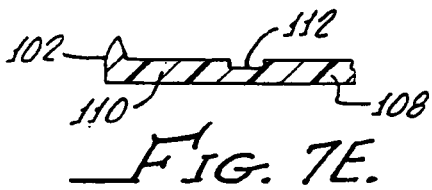
FIG. 7E is a sectional view taken through line 7E–7E of FIG. 7B.

With reference to FIGS. 7C and 7E, the intermediate members 106 comprise a radially inner portion 108, a radially outer portion 110, and a hinge 112 therebetween. The inner and outer portions 108, 110 are generally plate-like having larger circumferential dimensions then axial dimensions. The hinge 112 may be formed in a number of ways, and as illustrated comprises a region wherein both the axial and the circumferential thickness are reduced by about 50% with respect to the inner and outer portions 108, 110. The reduced material at the hinge 112 means that it is weaker than the remaining intermediate member and thus will more easily bend at that location. The location of each hinge 112 is desirably the same for all of the fixation intermediate members 106, and preferably is closer to the support ring 102 than to the optic 104. For example, each hinge 112 may be located about 60% of the way from the optic 104 to the support ring 102.

FIG. 7D illustrates the IOL 100 in elevational view wherein the support ring 102 lies substantially in a plane and the optic 104 projects in a posterior direction therefrom by virtue of the shape of the intermediate members 106. Specifically, the intermediate members 106 are bowed slightly in the posterior direction such that the optic 104 will tend to lie against or closely adjacent to the posterior wall of the capsular bag. As explained above, relaxation of the ciliary muscles surrounding the capsular bag either moves the optic 104 in the anterior direction or reduces the posterior bias imparted thereto by the intermediate members 106. As a result, the vitreous humor behind the capsular bag can move the optic 106 forward, or in the anterior direction.

In one exemplary embodiment, the support ring 102 has a diameter of between about 9.0–10.5 mm, and an axial thickness of about 0.7 mm. Furthermore, the support ring 102 has a curvature that mimics the curvature of the natural capsular bag between the anterior and posterior zonules, which curvature is between about 0.3–1.0 mm. As mentioned above, at least one corner edge of the outer ring is left sharp to help prevent cell growth thereon.

Although three radial intermediate members 106 are illustrated 120° apart, the configuration of the intermediate members 106 may vary. However, two factors that are believed to facilitate axial movement, or accommodation, of the optic 104 are the tripod orientation and presence of the hinges 112. More specifically, inward radial forces from the surrounding ciliary muscle and intermediary zonules are transmitted from the support ring 102 through the intermediate members 106 to the optic 104. Because the intermediate members 106 are oriented so that none is diametrically opposed to another, there are no directly opposing forces and a larger component therefore translates into axial movement of the optic 104.

The intermediate members 106 are plate-like to increase stability of the lens in the eye. That is, the forces imparted by the surrounding ciliary muscle may not be entirely uniform and may exert torsional forces on the lens. Plate-like intermediate members 106 help resist twisting of the lens and thus increases stability. The circumferential thickness, or width, of the intermediate members 106 may be between about 1.5–4.0 mm, and the axial thickness is desirably between about 0.2–0.5 mm.

FIG. 17 shows an alternate embodiment of an IOL 102' substantially similar to the embodiment of FIGS. 7A–7E, except that the thickness of the hinge portion 112' is reduced in the axial direction only. That is, the circumferential thickness, or width, of each plate-like intermediate member 106' is uniform throughout its length. This hinge configuration has been found to be less susceptible to fibrosis than a hinge configuration having reduced thickness in the circumferential direction.

Another alternative IOL 120 of the present invention is seen in FIGS. 8A–8D. As in an earlier embodiment, there are only two intermediate members 122 extending between an oval shaped outer capsular bag support ring 124 and an inner circular optic 126. In the illustrated embodiment, the outer ring 124 comprises a band having a generally rectangular cross-section with a longer axial than radial dimension. Preferably, at least one corner of the outer ring 124 is sharp to prevent epithelial cell growth thereon. The support ring 124, inner optic 126, and intermediate members 122 are firmly attached to each other with adhesive or ultrasonic bonding, or preferably formed integrally, i.e., molded or machined as a cohesive single piece. The IOL 120 is desirably liquid injection molded from silicone or machined from a hydrophilic material which, again, reduces cost and increases quality and/or consistency of the product.

Figure 8A:
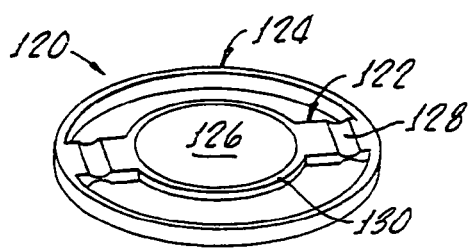
FIG. 8A is a perspective view of a still further alternative intraocular lens of the present invention having two radially oriented plate-like intermediate members connecting a central optic to an oval surrounding capsular bag support ring.
Figure 8B:
FIG. 8B is another perspective view of the intraocular lens of FIG. 8A.
Figure 8C:
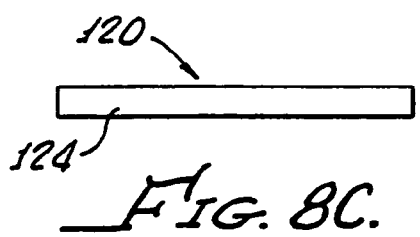
FIGS. 8C and 8D are side elevational and plan views, respectively, of the intraocular lens of FIG. 8A.
Figure 8D:
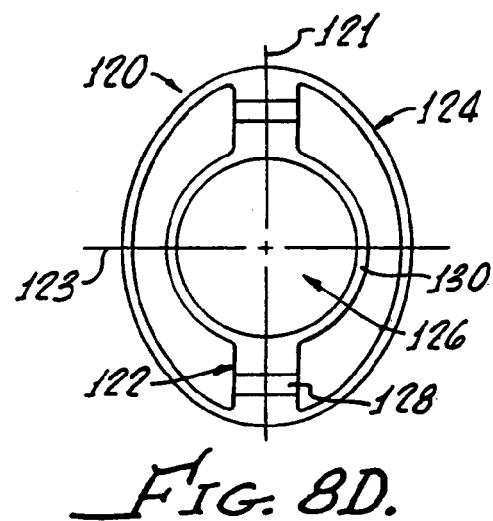

As seen best in FIG. 8D, the oval outer ring 124 has a major axis 121 and a minor axis 123, and the two intermediate members 122 are diametrically opposed across the optic 126 along the major axis 123. In one exemplary embodiment, the support ring 124 has a major diameter of between about 115–135% of the minor diameter.

The intermediate members 122 are plate-like, each having a relatively larger circumferential than axial dimension. In contrast to the IOL 100 of FIGS. 7A–7D, the intermediate members 122 lie in a plane defined by the oval-shaped outer ring 124, and thus the optic 126 is not bowed either way. Furthermore, the intermediate members 122 are joined to the inner surface of the outer ring 124 at approximately the axial midpoint thereof. Therefore, in contrast to the earlier embodiment, the optic 126 is not positioned or biased to favor movement in one direction or the other.

With reference to FIG. 8A, each intermediate member 122 has a hinge 128 therein located closer to the outer ring 124 than to the optic 126. The location of each hinge 128 is desirably the same for all of the intermediate members 122, and preferably is located about 75% or more of the way from the optic 126 to the support ring 124. Empirical determination of hinge 128 location optimizes the design such that less radial and axial compression force is required to axially translate the optic 126, while at the same time the ability of the lens to resist twisting is not adversely affected. In the illustrated embodiment, these hinges 128 are formed by reduced axial thickness portions along each intermediate member 122. For example, curved troughs on both sides of intermediate members 122 as shown may form the hinges. Alternatively, or in addition, the circumferential dimension of each intermediate member 122 may be reduced.

As with the earlier embodiment, the optic 126, whether it be biconvex or otherwise, is recessed from a circular rim 130 to which the intermediate members 122 are directly attached. The rim 130 is slightly tapered downward toward the optic and helps reduce glare on the lens. Desirably, the maximum axial dimension of the rim 130 is greater than the center thickness of the optic 126. Advantageously, a reduced center thickness permits a reduction in incision size.

Figure 18A:
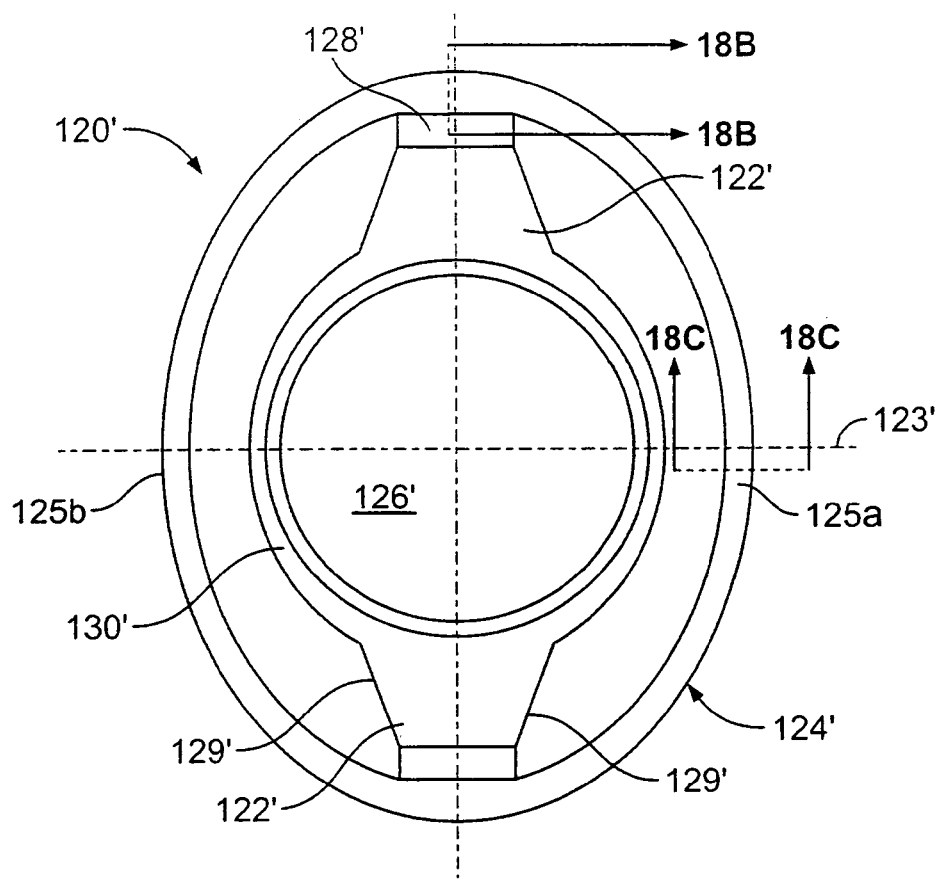
FIG. 18A is an anterior plan view showing yet another embodiment of an intraocular lens according to the present invention.
Figure 18B:
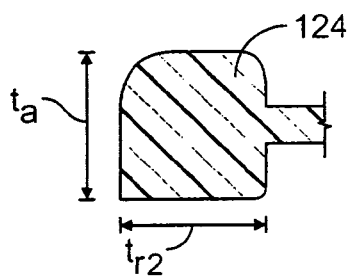
FIG. 18B is a sectional view taken through line B—B of FIG. 18A.
Figure 18C:
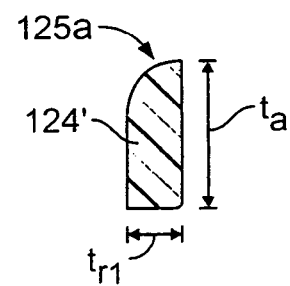
FIG. 18C is a sectional view taken through line C—C of FIG. 18A.

FIGS. 18A–18C show an alternate embodiment of an IOL 120' similar to the embodiment of FIGS. 8A–8D, except that the oval support ring 124' has a non-uniform cross-sectional area. Specifically, the radial thickness of the support ring 124' increases from a minimum value $t_{r1}$, for instance about 0.2 mm, at diametrically opposed locations 125a and 125b along the minor axis 121', to a maximum value $t_{r2}$, for instance about 0.6 mm, at diametrically opposed locations along the major axis 123', where the intermediate members 122' are secured to the ring 124'. In addition, the axial thickness $t_a$ of the ring 124' is constant throughout the entire circumference of the ring 124' and has a value greater than the maximum radial thickness $t_{r2}$.

The circumferential thickness, or width, of each intermediate member 122' is also non-uniform throughout its length, for instance decreasing in a non-linear fashion from a maximum width where the intermediate member 122' joins the circular rim 130' of the optic 126' to a minimum width at the hinge 128', and remaining substantially constant between the hinge 128' and the outer ring 124'. This particular configuration of the oval outer ring 124' and intermediate members 122' has been found to be particularly stable, with minimal "flopping", twisting, or other unwanted movement, of the thinnest portions 125a and 125b of the ring 124.

FIGS. 9–16 and 19 show alternate embodiments of the invention wherein the support ring includes weakened portions configured to allow the ring to allow consistent and repeatable deformation during compression.

Figure 9:
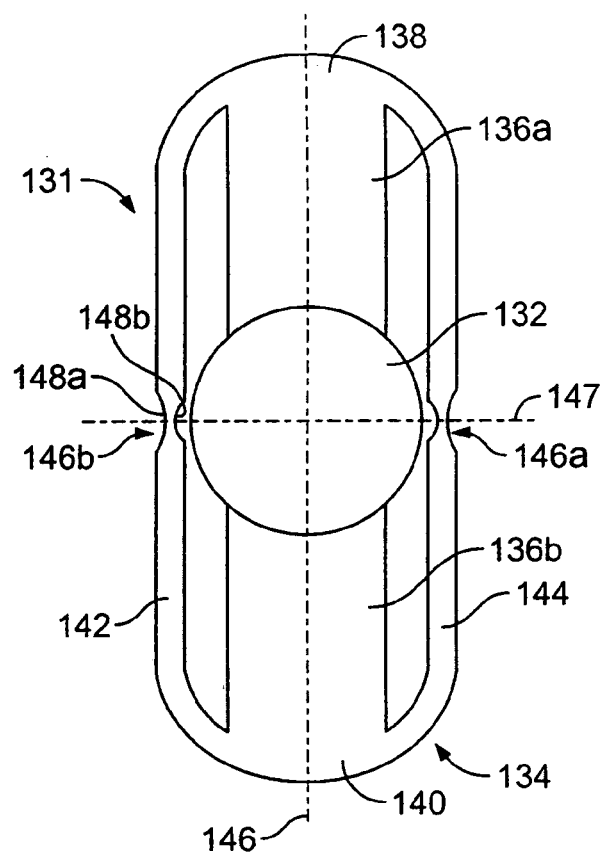
FIG. 9 is a plan view of another alternate embodiment of the invention.

FIG. 9 shows an IOL 131 having an optic 132, an outer ring 134, and a pair of plate-like intermediate members 136a and 136b. The intermediate members 136a and 136b are shown without hinges, similar to the intermediate members 76a and 76b of FIG. 4, although hinged intermediate members could also be used. The outer ring 134 is generally oval, with two generally arcuate ends 138, 140 that merge with the distal ends of the intermediate members 136a and 136b, respectively, and two elongated leg portions 142, 144 that extend parallel to a major axis 146 of the outer ring 134 along opposite sides of the optic 132.

A weakened portion 146a, b is formed in each leg portion 142, 144 at a location along the minor axis 147 of the support ring 134, such that each weakened portion 146a, b is 180° away from the other weakened portion 146a, b and equidistant from the arcuate ends 138, 140 of the outer ring 134. Each weakened portion 146a, b is in the form of a thinned area in one of the legs 142, 144, the thinned area being created, in this embodiment, by providing a generally C-shaped indentation 148a, b on each side of the leg. This configuration ensures that any bending or buckling of the outer ring 134 as a result of compressive forces on the distal ends 138, 140 of the outer ring 134 will occur at the weakened portions rather than elsewhere.

Figure 10:
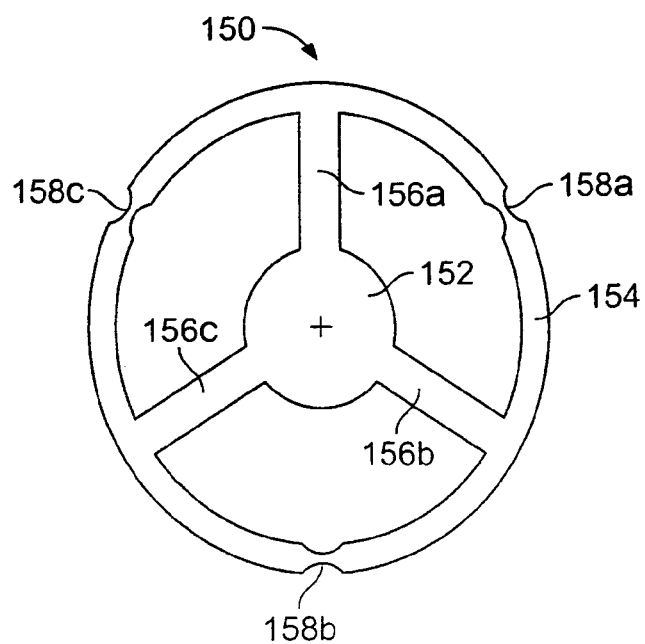
FIG. 10 is a plan view of still another alternate embodiment of the invention.

FIG. 10 shows an IOL 150, generally similar to IOL 80 of FIG. 5, comprising an optic 152, a circular outer ring 154 and three evenly arranged and radially oriented intermediate members 156a, 156b, and 156c, which may be hingeless as shown, or hinged, as in the embodiment of FIGS. 7A–7D. The support ring 154 includes three weakened areas 158a, b, c provided 120° from one another and radially equidistant from the intermediate members 156a, 156b, and 156. Again, the weakened areas 158a, b, and c. which are shown here as C-shaped indentations on each side of the ring 154, are configured to ensure that any bending or buckling of the ring 154 occurs at the three weakened area only, rather than at other locations along the ring.

Figure 11:
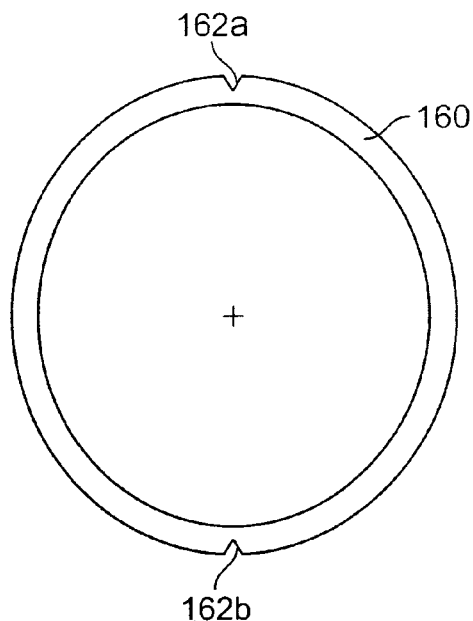
FIG. 11 is a plan view of an outer ring according to yet another embodiment of the invention.

FIG. 11 shows an outer ring 160 according to an alternate embodiment of the invention wherein the weakened areas 162a and 162b are in the form of V-shaped indentations or grooves in the outer circumferential surface 163 of the outer ring 160. An outer ring 160 having this configuration will tend to bend or buckle in a radially inward direction at the two weakened areas 162a and 162b when the outer ring 170 is subjected to compressive forces.

Figure 12:
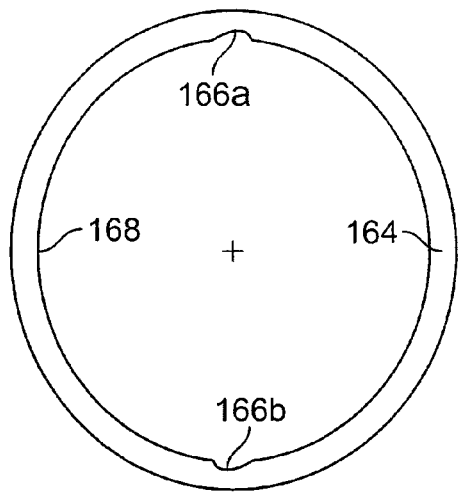
FIG. 12 is a plan view of an outer ring according to another embodiment of the invention.

FIG. 12 shows an outer ring 164 according to another embodiment of the invention wherein the weakened areas 166a and 166b are in the form of U-shaped indentations or grooves formed in the inner circumferential surface 168 of the outer ring 164. An outer ring 164 having this configuration will tend to bend or buckle in a radially outward direction at the two weakened areas 166a and 166b when the outer ring 164 is subjected to radially compressive forces.

Figure 13:
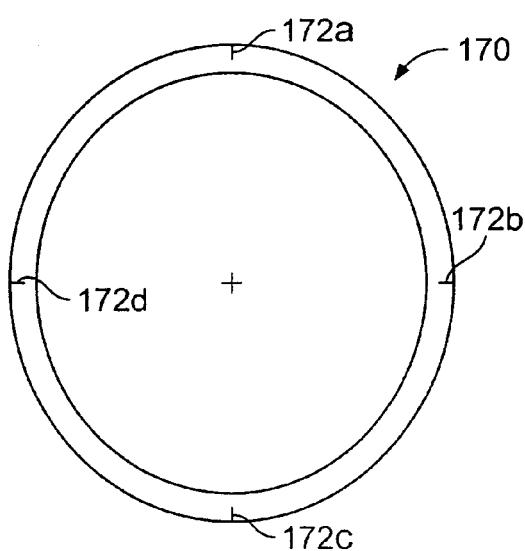
FIG. 13 is a plan view of a outer ring according to still another embodiment of the invention.

In still another embodiment of the invention, shown in FIG. 13, the outer ring 170 is provided with four symmetrically arranged weakened areas 172a, b, c, and d, each in the form of a slit or notch in the outer circumferential surface 174 of the outer ring 170. An outer ring 170 having this configuration will tend to bend or buckle in a radially inward direction at the four weakened areas when the outer ring 170 is subjected to radially compressive forces.

Figure 14:
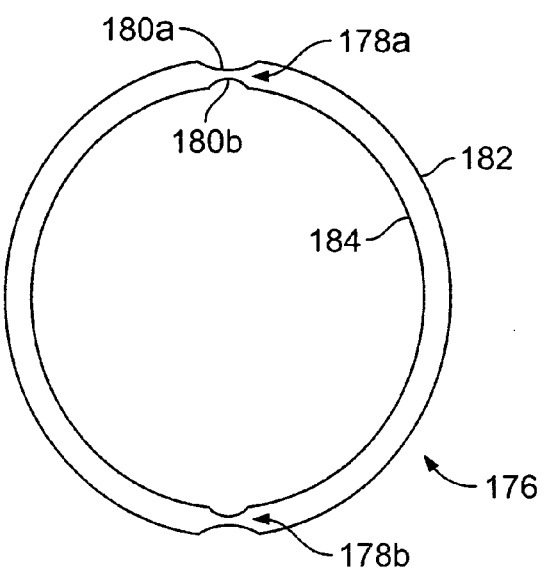
FIG. 14 is a plan view of a outer ring according to still another embodiment of the invention.

In yet another embodiment, shown in FIG. 14, a circular outer ring 176 is provided with two thinned areas 178a and 178b on diametrically opposite locations on the ring. Each thinned area is formed by providing a pair of U-shaped grooves or indentations in the ring 176, each pair consisting of a first indentation 180a in the outer circumferential surface 182 of the outer ring 176 and a second indentation 180b in the inner circumferential surface 184 of the outer ring 176.

FIG. 15 is an enlarged fragmentary perspective view showing a weakened portion 186 according to still another embodiment of the invention. In this embodiment, the weakened portion 186 comprises a thinned area, notch, indentation or groove formed in the posterior face 188 of the outer ring 190. An outer ring 190 having a plurality of weakened portions 186 configured in this way will tend to bend in an anterior direction (towards the cornea) at each of the weakened portions when subjected to radially compressive forces.

Alternatively, a weakened portion 192 according to another embodiment of the invention may comprise a thinned area, notch, indentation or groove formed in the anterior face 194 of the outer ring 196, as shown in FIG. 16. An outer ring 196 having a plurality of weakened portions 192 configured in this way will tend to bend in an posterior direction (away from the cornea) at each of the weakened portions when subjected to radially compressive forces.

Figure 19:
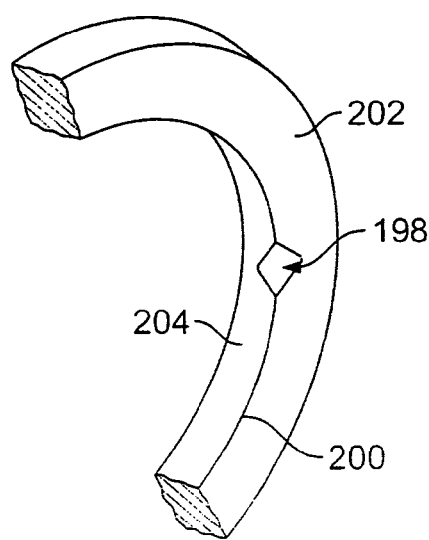
FIG. 19 is a fragmentary perspective anterior view showing a support ring structured to bend both posteriorly and radially outwardly.

FIG. 19 shows yet another embodiment of the invention wherein a weakened portion 198 is configured to cause bending in both a posterior and a radially outward direction. Although the weakened portion 198 is shown as a single notch formed at the corner 200 between the anterior surface 202 and the inner circumferential surface 204, it could also be formed as a pair of intersecting notches, grooves or indentations, one extending entirely across the anterior surface 202 and the other extending entirely across the inner circumferential surface 204, or any other equivalent configuration.

A weakened portion or portions could also be formed on any other combination or intersection of surfaces, for instance at a corner between a posterior surface and an outer circumferential surface to cause bending in anterior and radially inward directions, or at a corner between an anterior surface and an outer circumferential surface to cause bending in posterior and radially inward directions. Various other combinations of weakened portions will be readily apparent to the skilled practitioner, but for reasons of brevity will not be illustrated here.

The configuration, number and location of the weakened portions in each of the illustrated embodiments are intended merely to be illustrative and, in practice, will depend on various factors such as the number and configuration of the intermediate members, the materials used, and the mode of deformation desired.

Furthermore, the outer rings and intermediate members in the IOLs of the embodiments in each of the FIGS. 1–17 are not intended to be limited to use with optics of any particular structure or type of material. For instance, the optics may be formed of rigid biocompatible materials such as polymethyl methacrylate (PMMA) or deformable materials such as silicone polymeric materials, acrylic polymeric materials, hydrogel polymeric materials, and the like. In addition, the optic bodies may be either refractive or diffractive.

In the most preferred embodiments, the optic body has a diameter in the range of about 3.5 to about 7 mm and, optimally, in the range of about 5 mm to about 6 mm. The overall diameter of the IOL, including the intermediate members and outer ring in unstressed conditions, is preferably about 8 mm to about 13 mm. Additionally, the optic has a far-vision correction power for infinity in an unaccommodated state.

While the present invention has been described with respect to various specific examples and embodiments, it is to be understood that the invention is not limited thereto and that it can be variously practiced within the scope of the following claims.

What is claimed is:

1. An intraocular lens for insertion into a capsular bag of an eye, comprising:
an optic having a periphery and centered on an optical axis, the optic adapted to focus light toward a retina of an eye;
a continuous outer ring surrounding the optic and spaced therefrom with voids therebetween; and
a plurality of intermediate members extending between and connecting the optic and the outer ring, each intermediate member of the plurality of intermediate members attached to the periphery of the optic along a radial line passing through the optical axis and through the center of the intermediate member having a hinge that is located closer to the outer ring than to the optic.

2. An intraocular lens for insertion into a capsular bag of an eye, comprising:
an optic having a periphery and centered on an optical axis, the optic adapted to focus light toward a retina of an eye;
a continuous outer ring surrounding the optic and spaced therefrom with voids therebetween; and
a plurality of intermediate members extending between and connecting the optic and the outer ring, each intermediate member of the plurality of intermediate members attached to the periphery of the optic along a radial line passing through the optical axis and through the center of the intermediate member, the optic being a multifocal optic.

3. The lens of claim 2, wherein the optic has a maximum add power that is less than the full add power required for an otherwise identical optic that has not been adapted for accommodating movement.

* * * * *